(12) United States Patent
Padgett et al.

(10) Patent No.: US 8,296,983 B2
(45) Date of Patent: Oct. 30, 2012

(54) IDENTIFICATION BRACELET WITH INTERCHANGEABLE SEGMENTS PROVIDING USER SELECTABLE SIZING

(75) Inventors: John M. Padgett, Clermont, FL (US); Michael G. Jungen, Orlando, FL (US); John David Worrall, Clermont, FL (US); Maximillian Philip Burton, San Francisco, CA (US); Carson Lau, San Francisco, CA (US); Adam D. Leonards, El Cerrito, CA (US)

(73) Assignee: Disney Enterprises, Inc., Burbank, CA (US)

( * ) Notice: Subject to any disclaimer, the term of this patent is extended or adjusted under 35 U.S.C. 154(b) by 465 days.

(21) Appl. No.: 12/714,965

(22) Filed: Mar. 1, 2010

(65) Prior Publication Data

US 2011/0209374 A1    Sep. 1, 2011

(51) Int. Cl.
*A44C 5/00* (2006.01)
(52) U.S. Cl. .............. 40/633; 40/665; 59/80; 63/15.7
(58) Field of Classification Search ............ 40/665, 40/633
See application file for complete search history.

(56) References Cited

U.S. PATENT DOCUMENTS

| | | | | |
|---|---|---|---|---|
| 1,440,230 | A * | 12/1922 | Mestekin | 59/80 |
| 3,604,203 | A * | 9/1971 | Hofmann | 59/80 |
| 3,780,469 | A * | 12/1973 | Hancovsky | 446/127 |
| 4,742,503 | A | 5/1988 | Braun et al. | |
| 4,906,025 | A | 3/1990 | Schreindl | |
| 5,065,376 | A | 11/1991 | Choulat | |
| 5,416,953 | A | 5/1995 | Hui | |
| 6,450,402 | B1 * | 9/2002 | Regev | 235/375 |
| 7,041,032 | B1 | 5/2006 | Calvano | |
| 7,348,888 | B2 | 3/2008 | Girvin | |
| 7,481,370 | B2 | 1/2009 | Davis | |
| 2003/0159463 | A1 * | 8/2003 | Rosenberg | 63/15.7 |
| 2005/0108912 | A1 | 5/2005 | Bekker | |
| 2009/0096614 | A1 | 4/2009 | Singleton et al. | |

FOREIGN PATENT DOCUMENTS

WO    WO 2005027677 A2 *    3/2005

OTHER PUBLICATIONS

Wristloks, http://www.adsources.com/CATALOG/wristlocks.htm, retrieved on Dec. 14, 2009, Wristlocks Wristbands.
Synometrix, http://www.synometrix.com/china_taiwan_rfid_bracelets.shtml, RFID Wristbands & RFID Bracelets & FRID Bracelet Manufacturers China Asia, retrieved on Dec. 14, 2009.

* cited by examiner

*Primary Examiner* — Casandra Davis
(74) *Attorney, Agent, or Firm* — Marsh Fischmann & Breyfogle LLP; Kent A. Lembke (57) ABSTRACT

A wearable band with an adjustable size or length. The band includes a base band element with an elongated, thin body extending a first length from a first sidewall to a second sidewall. The body may include a user identification member that stores user ID information for a wearer of the band. The band includes a band sizing assembly with one, two, three, or more band sizing segments that are detachable linked together such as via a tongue and groove interlocking mechanism. The band sizing assembly extends a second length from first sidewall to a second sidewall, and these sidewalls are configured for coupling or linking with the sidewalls of the base band element body so as to form a closed loop or bracelet with a third length. A user may size the band by selecting the number and size of the sizing segments used in the band sizing assembly.

19 Claims, 7 Drawing Sheets

IDENTIFICATION BRACELET WITH INTERCHANGEABLE SEGMENTS PROVIDING USER SELECTABLE SIZING

BACKGROUND

1. Field of the Description

The present description relates, in general, to wearable bands or bracelets such as wristbands that are adjustable in size and that may be worn or used as user identification (ID) bracelets, and, more particularly, to wearable band assemblies that include a multi-sizing mechanism provided by a base (or identification) band element and a band sizing assembly with interchangeable segments, that allows the band to be sized in a tool-less manner by a user or wearer.

2. Relevant Background

Bands such as wristbands are worn in numerous settings. For example, watches have typically been worn on a wrist through the use of a wristband. In hospitals, patients often are provided an identification bracelet, strap, or band that they wear on their wrist. An amusement or theme park may provide a visitor or guest with a wristband that includes identification information or technology (e.g., a readable bar code, a radio frequency identification (RFID) transceiver or module, or the like) that identifies the visitor and allows the visitor to access the park's facilities. Often, bands are worn as fashion accessories or to allow the wearer to make a statement (e.g., to support a cause such as medical research, a political candidate, a sports team, or the like). It is likely that the demand for wearable bands such as wristbands or bracelets will continue to grow in the coming years.

One ongoing challenge for the makers of wristbands and other wearable bands is providing proper sizing for the end users. For example, most multi-size wristwatches include a first band portion that is attached at a first end to the timepiece and at a second end may have a number of spaced apart holes. A second band portion is attached at its first end to the timepiece and at its second end may contain a buckle-style clasp mechanism for mating with the holes of the first band portion. A person uses the clasp mechanism to both size the band about their wrist and to also lock the timepiece to their wrist. The wristwatches are multi-size only in that the spaced apart holes allow the same wristwatch to be worn by a set of people whose wrists have a size that falls within a predefined range (e.g., a minimum and maximum sized wrist diameter defined by the first and last holes on the band).

However, people outside this predefined range would not be able to wear the wristwatch as the overall length of the watch band is not readily adjusted, and the wristwatch manufacturer either simply loses these sales or may provide additional wristwatches that have different size ranges to suit these other buyers. Unfortunately, this requires added inventory that may or may not be sold. Some efforts have been made to provide band designs that allow the band to be sized for a particular person and the size of their wrist, but these designs typically require specialized tools to adjust the band and are expensive to manufacture. In other cases, a band selected for a user to match their wrist size may be attached by a retailer to the timepiece, but, again, this typically requires a special tool for attachment of the band to the timepiece and may require the buyer to have the watch sized by a trained technician.

As another example of the use of wearable bands, RFID wristbands are commonly used in hospitals and entertainment venues to identify individual patients and guests. The wristband may include or provide a communicative link to a variety of information such as the person's name, their room number, a seating location for a show, entitlements permitted in the hospital or venue, and so on. The wristband is often designed to be secured or locked onto the wrist of the person during their stay at the hospital or participation in an entertainment event.

While these wristbands have been useful in identifying the patients and guests, their design has typically not effectively accommodated the wide range of users' wrist sizes, which has resulted in many users having very loose or too tight and uncomfortable fitting wristbands. Additionally, many wristband designs use either an adhesive closure that is peeled away from the wristband or a separate, one-time plastic snap closure. The adhesive closures sometimes do not provide the closing strength desired and once removed, cannot be worn again. The plastic snap closures provide greater closing strength but often are intentionally designed for one time use, which limits use of these bands on an ongoing or repeated basis. Further, the snap closures often do not support a large enough range of wrist sizes such that they are often too tight or cannot be worn comfortably or are too loose which may allow them to fall off.

Accordingly, there remains a need for a low cost, multi-sizing mechanism for RFID wristbands and other wearable bands or bracelets. The band designs preferably would have durable opening and closing features to allow reuse of the band and would support relatively inexpensive manufacture from a variety of available materials such as plastics, silicones, metals, and/or other materials used presently (and in the future) for wearable bands. Further, there is a need for such a multi-sizing mechanism to be more fully adjustable to the wearer's wrist size, to provide a secure fastening mechanism that during regular wear can be fastened and unfastened by the wearer with ease, and to provide an aesthetic appearance that accommodates different wrist sizes within a large audience or wearer demographic.

SUMMARY

To address the above and other problems with wearable bands such as identification (ID) bands, a wearable band design is provided that allows a wearer to easily adjust the size of the band (or ID bracelet) to suit the size of their wrist (or other body part such as the ankle or neck). Generally, a wearable band assembly is provided that includes a base band element that may include user ID technology (e.g., an RFID module or the like embedded in the band body). To allow a user to size the band assembly, a band sizing assembly is provided that may include one, two, three, or more segments or links, and the user may choose a set of these segments that provides the proper overall length for the band assembly when combined with the base band element. The base band and the sizing segments are configured to be interlocked along their sidewalls or ends of their bodies, such as via an alternating tongue and groove arrangement that allows adjacent or abutting sidewalls to be snap locked or press fit together.

When the base band and one or more sizing links are combined, the band assembly may be worn by one or more wristband sizing ranges (or users having varying wrist sizes). The base band, which may include an RFID module or other user ID technology, may be provided with a standard length or size while the additional sizing segments may come in one, two, or more lengths or sizes with each segment having an interlocking fastening mechanism (or half of such mechanism with an adjacent segment or base band providing the other half of the mechanism, e.g., one segment sidewall provides a groove while the other segment sidewall or base band side/edge provides a post or a tongue to mate with the groove) that attaches the segments together to form a wearable band or bracelet. Depending upon an end user's wrist size, they can add or remove sizing segments of one or more sizes to build a band or bracelet that fits their specific wrist size. Hence, the segmented ID band or bracelet allows for one segment or base band element to provide the user ID member or device that is fully interchangeable or useful with a wide variety of sizing segments of a band sizing assembly. The sizing segments may be thought of as product modules as they may be selected based on their particular design and not just their function, e.g., based on the graphical content, color, material(s), and so on rather than just on size or length and a coupling mechanism.

It was recognized that prior techniques of providing multi-size wristbands and similar products seemed to either require large inventories or provided a disposable wristband that provided no ongoing revenue source (or source of additional product sales). The wearable band assemblies described herein provide a product platform in that they typically include a base portion (e.g., a band element with an RFID or other information technology component) and an interchangeable extending or sizing portion (e.g., band sizing assembly that may include one or more sizing segments or links) that may be selected or built by the user to provide a desired size/length extension and then readily attached and detached from the base portion.

In this manner, the wristband assembly permits interchangeability with a wide range of wearable styles of merchandise product offerings as the sizing segments may be sold or distributed separately from the base portion so as to allow a user/wearer to later purchase differing band elements to personalize or modify their wristband or wearable band assembly. The base or identification band element, though, may be provided in a single (or limited number) of designs to simplify its design and reduce cost of its manufacture and distribution (or inventory costs as only one to several choices may be provided), and manufacturing may also be simplified by selling a single wearable band assembly that may include a base band element along with a band sizing assembly, which provides the user with sizing segments to build two, three, four, or more differing bands with differing lengths and/or differing appearances (e.g., differing segments with the same size/length may be used to create bands with differing appearances).

More particularly, a wearable band is provided with an adjustable size or length. The band includes a base band element with an elongated, thin body extending a first length from a first sidewall to a second sidewall. The body may include a user identification member (e.g., an RFID module or tag) that stores user ID information and/or other information for a wearer of the band. The band further includes a band sizing assembly with one or more band sizing segments linked together. The band sizing assembly extends a second length from a first sidewall to a second sidewall, and these sidewalls are configured for coupling or linking with the sidewalls of the base band element body so as to form a closed loop or bracelet with a third length (e.g., a circumference of the closed loop or bracelet).

The coupling between the first sidewalls and between the second sidewalls may be a tongue and groove type connection with each pair of linked sidewalls including a tongue extending from one sidewall and a groove or slot for receiving this tongue provided in the other sidewall. The tongue and grooves may extend along the sidewall (e.g., transverse to the longitudinal axes of the base band element body and the segment bodies) and, in some cases, have circular sectional shapes. The diameter of such circular cross section may be uniform or tapered (increasing in diameter for the tongue and decreasing in diameter for the groove). In some cases, a stop surface is provided on each sidewall such as about at a midpoint and the tongues/grooves only extend from an outer edge of the link/segments bodies to the stop surface, and, when linked together, the segments have the stop surfaces in abutting contact. In some embodiments, a snap or lock fit is provided by providing a rib or other raised surface(s) on the tongue and a recessed surface corresponding in size and location to the rib in the groove, whereby when the tongue is fully inserted into the groove or slot the rib is received within (or snapped into) the recessed surface, and a user has to apply a force to disassemble the linked segments.

The band sizing assembly may include first and second sizing segments or links that may be detachably engaged with each other such as with tongue and groove components provided on their endwalls or sidewalls. The length of the first sizing segment may differ from the length of the second sizing segment, and, in some embodiments, third, fourth, or more sizing segments are included and each may have differing or the same body length such that a user may size the band assembly by inclusion of a particular number of sizing segments.

DETAILED DESCRIPTION OF THE PREFERRED EMBODIMENTS

The following description is generally directed toward a wearable band such as a wristband that may be readily configured to one of two or more sizes by choosing among one, two, or more sizing segments from a band sizing assembly and using these segments along with a base band or base band element to build a segmented band. FIGS. 1-7 illustrate several embodiments of such a wearable band, but, prior to describing these band embodiments, it may be useful to more generally describe exemplary wearable bands (which may also be called wristbands or segmented bracelets herein for simplicity of explanation without being limited to use on a wrist) and advantages of such bands when compared with existing bands or straps. Additionally, the following description highlights use of the bands as RFID wristbands or user ID bracelets, but it will be understood based on the description that the bands or bracelets can readily be used with nearly any identification technology (such as barcodes or the like) as well as for bands without identification technologies/readable information. For example, the bands may be used with timepieces/watches or as products worn for fashion or other reasons.

Generally, the wearable bands described herein are designed to address or solve the multi-sizing and fastening mechanism problem that faces makers of wrist and other bands. The bands are easy for end users to assemble or configure into a particular size and allow interchanging of base band elements and/or sizing segments to personalize the bands. The bands are also adapted to make manufacture relatively inexpensive as the segmented design provides a base band component or element that contains the identification module such as RFID tag or module and a band sizing assembly. The base band element and the band sizing assembly, with user chosen sizing segments, are coupled together and function together to provide a multi-size band that can be used by all or a large portion of the population. The supply chain is also simplified in this manner as one or several base designs may be offered to the consumers, who can optionally personalize their bands by which sizing segments they include in their band and/or by purchasing personalized/customized portions of the band (e.g., replacing all or portions of the band sizing assembly or even, in some cases, the base band element).

Figure 2:
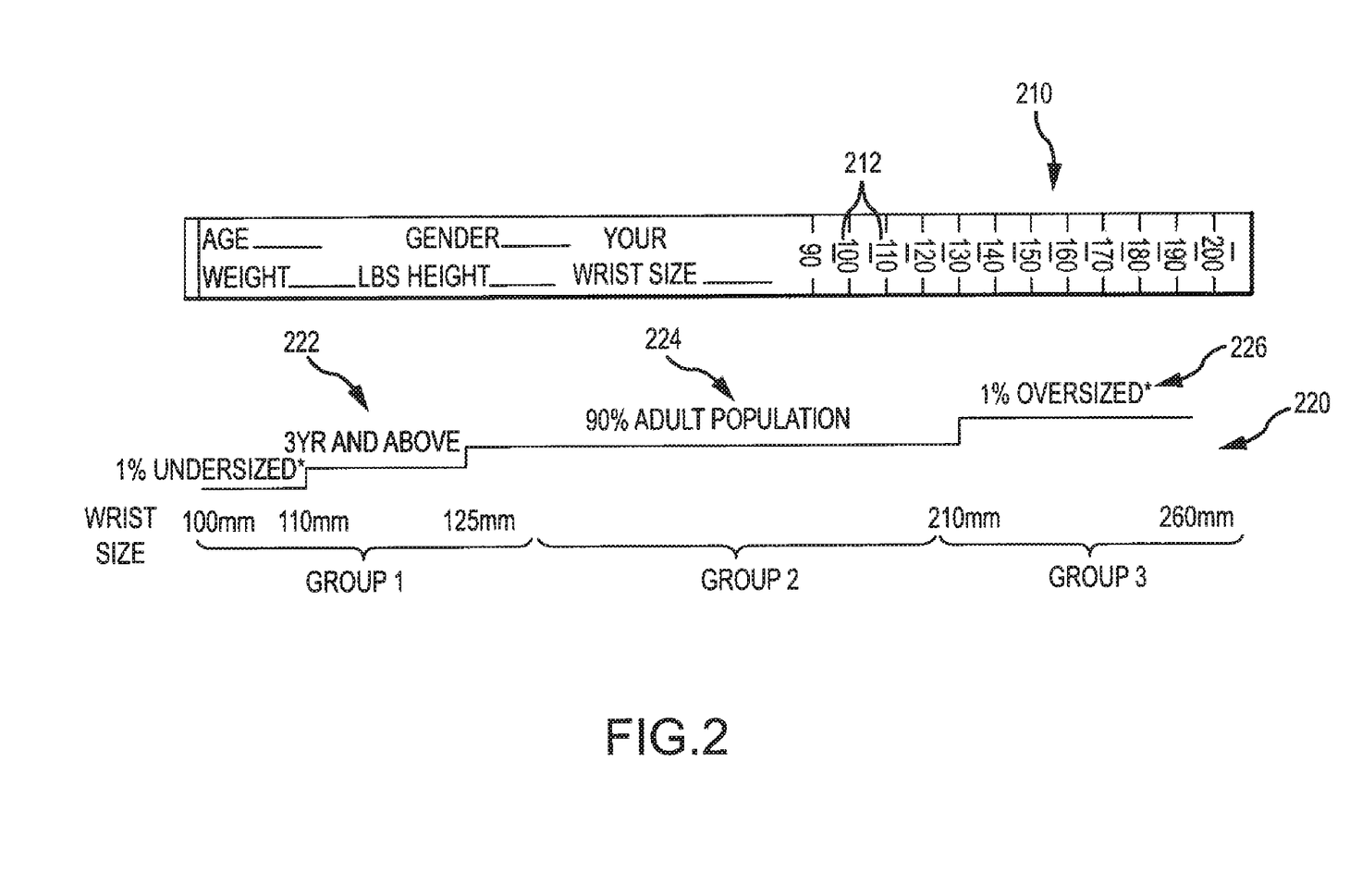
FIG. 2 illustrates a tape measure or tool that may be used by a purchaser/wearer of a band assembly to size their wrist and further illustrates a graph showing grouping of wrist sizes or ranges of wrist sizes to correspond to lengths/sizes of a band assembly (such as the assembly of FIG. 1) via inclusion or exclusion of a number of particular sizing segments or extensions to achieve a particular size (e.g., inner "diameter" or overall length of the components that combine to define the dimensions of the band)
Figure 3:
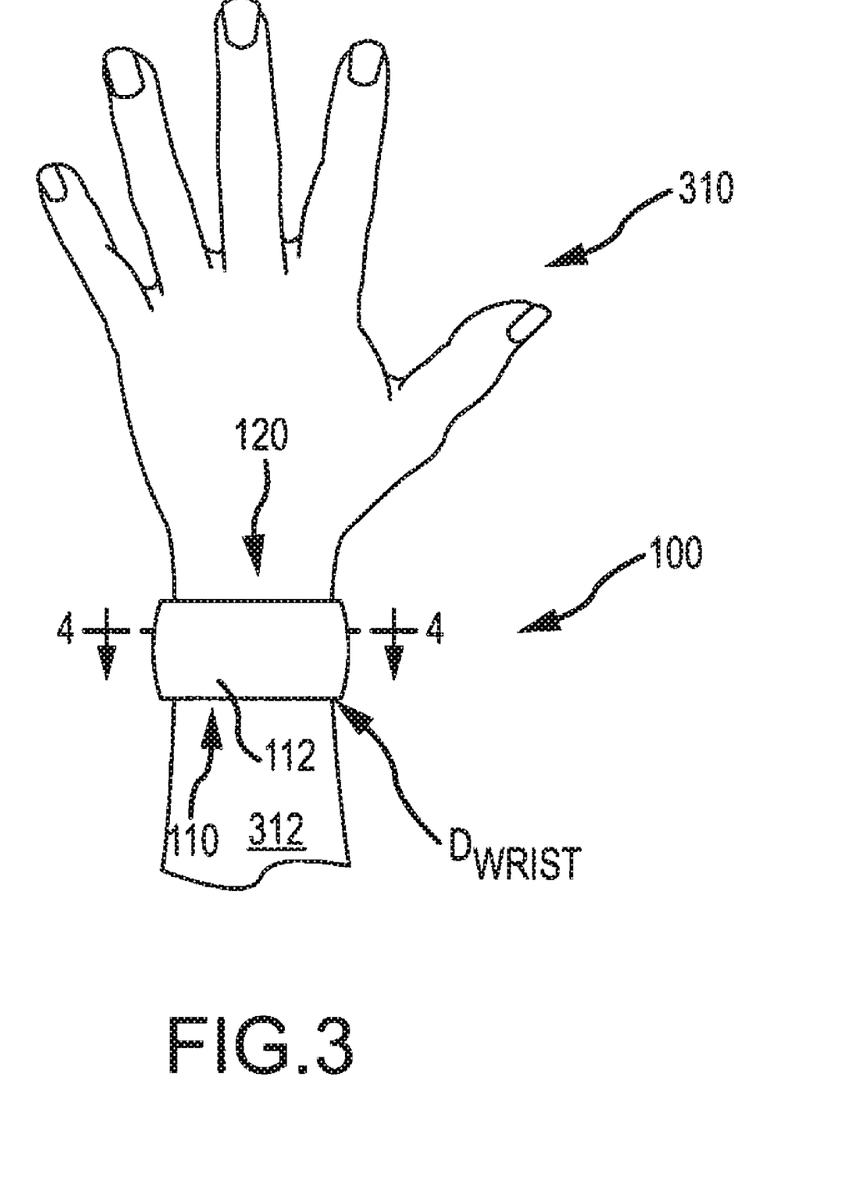
FIG. 3 illustrates a user or wearer wearing the band assembly shown in FIG. 1 with three sizing segments included (as visible in FIGS. 1 and 4) so as to size the band assembly to the wrist of users/wearers (e.g., including more and/or longer segments increases the size of the band while removing or not including segments or choosing shorter segments reduces the size of the band)

In one example, an adjustable RFID wristband or user ID bracelet is provided that can be manufactured from a variety of modern day materials including plastics, rubbers, and silicones and even, in some cases, metals, leathers, cloths/textiles, and other materials. The wristband is fully adjustable by the wearer to suit their wrist size and also provides an aesthetic appearance. The wristband is also adapted to provide a secure wristband fastening mechanism that during regular wear can be fastened and unfastened by the wearer with exceptional ease (e.g., the band supports reuse rather than being a one-time product as was the case with many prior one-size-fits-all straps). This embodiment may be thought of as providing a band assembly made up of a two or more piece band design including a base or identification band element and a band sizing assembly made up of two, three, or more sizing segments. Each segment in the band sizing assembly may be retained or removed to allow the wristband to cover or be used with a defined wristband size range or wrist size range (see FIGS. 2 and 3 showing exemplary sizing groups and an assembled wristband worn on a user's wrist).

Prior to the band designs presented herein, many wristbands used either an adhesive closure that is peeled away from the wristband or a separate, one-time plastic snap closure. The adhesive closures sometimes did not provide a desired closing strength and once removed could not be worn again. The plastic snaps provided a greater closing strength but were also often designed for one-time use, did not fit the wearer comfortably, and/or were too loose. With regard to other band applications, a typical wristwatch incorporates a buckle-style watch clasp. Similar to shoe manufacturing, most wristwatches are designed to a particular style with that same style or product run having a variety of wristwatch bands in different sizes to accommodate the specific end users' wrist sizes. However, similar to shoe shopping, when an end user purchases a wristwatch they try on different sizes of wristwatches (or wristwatch bands) of the same style to determine which band fits them appropriately. Because of the variability of different end user wrist sizes, the watch retailer must keep a large inventory of different wristband sizes to accommodate their customers, which significantly increases inventory costs for the retailer that may be acceptable in some settings (such as for higher end band products such as certain wristwatches).

However, in many fashion and wearer ID settings (such as entertainment venues and the like), it is much more desirable to be able to provide a one-size-fits-all solution or band design that can be sized by the seller or the wearer to suit their wrist size rather than carrying numerous versions/sizes of the band. The described wearable bands provide a "one size fits all" design that provides at least two and sometimes three or more wearable and user-selectable/interchangeable band sizing segments or links in a band sizing assembly (e.g., the product or extension portion of the band design). This configuration allows a venue operator or provider of bands to maintain one common base band (e.g., the intelligence or ID portion of the two-piece band) inventory and one or more sizing band sizing assemblies that together accommodate a wide range of wrist sizes (e.g., address the multi-sizing problem associate with serving large audience/customer bases). In some case, a user of the wristbands or bracelets may even be able to interchange single sizing segments or links to personalize or customize their wristband or bracelet.

Figure 1A:
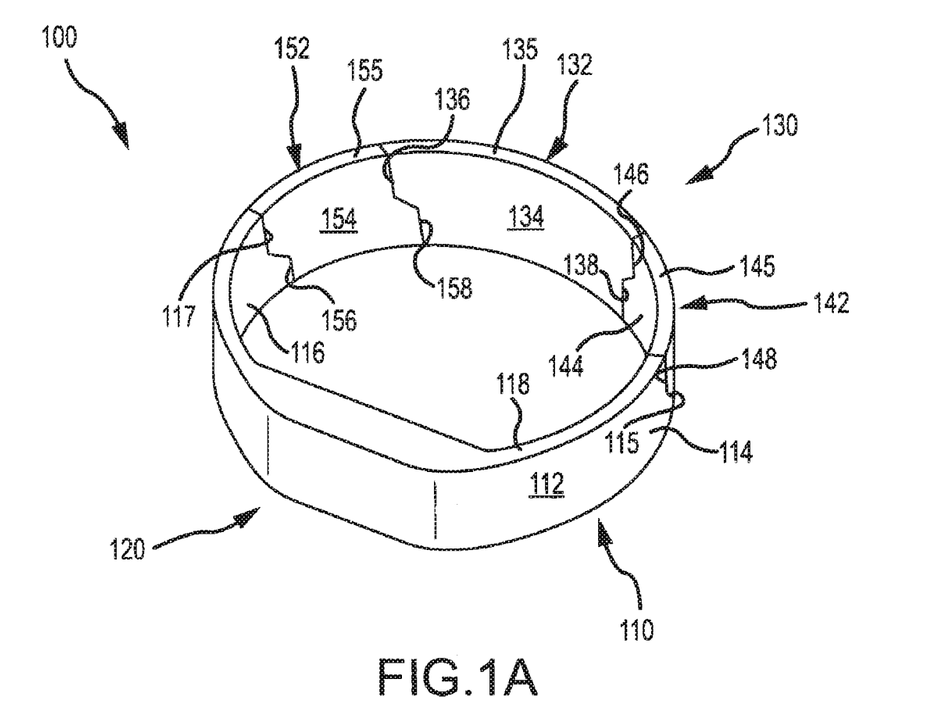
FIGS. 1A and 1B are top front and top rear perspective views of a wearable band assembly of an embodiment of this description as it may be assembled with a base band element along with one or more (three shown) segments or extensions as part of a band sizing assembly to have a desired size for a user (and personalization/customization in some cases by selecting/substituting the particular sizing segments or extensions)
Figure 1B:
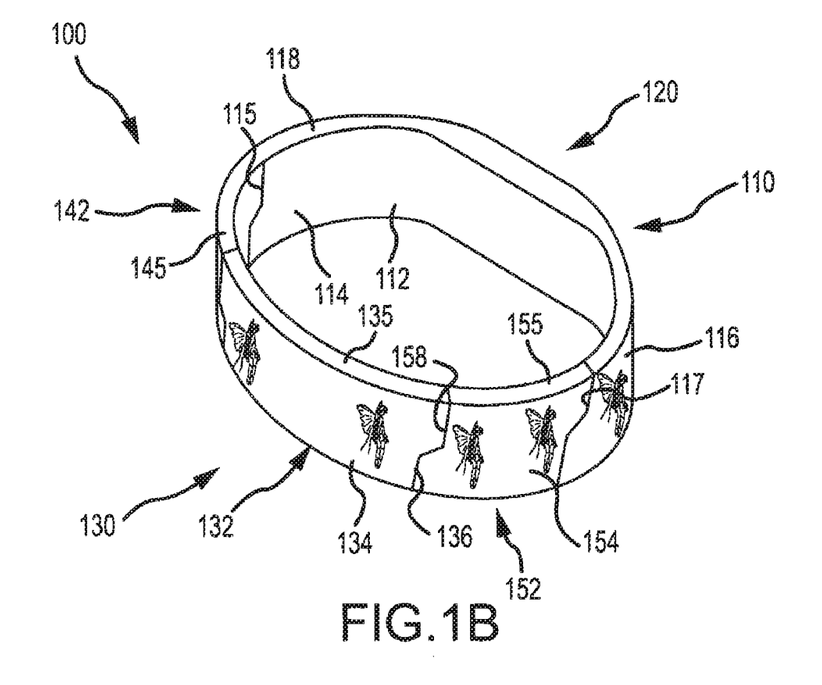

FIGS. 1A and 1B illustrate one embodiment of a wearable band assembly 100 that may be used to provide a single band or bracelet product that can be worn or used by people (i.e., wearers or users) with wrist sizes that fall within one of two, three, or more predefined size groups (e.g., may vary significantly and still use a single bracelet design). The band assembly 100 may be thought of as providing a interchangeable segment band design that includes a base band or base band element 110 and a band sizing assembly 130. As will become clear from the following description, the base band 110 is included in each configuration of the wearable band assembly 110 while sizing is provided by modifying the band sizing assembly 130 by the selection of which sizing segments to include in the assembly 100. The segmented sizing assembly 130 is interconnected to the base band 110 to form the wrist band assembly as shown that may be slid over a user's wrist.

The band element 110 may be thought of as the base or, in some cases, intelligence (or ID) band or component as this typically larger link/segment is included in each configuration of the segmented band assembly 100. The base band 110 has a body 112 that extends from a first end 114 to a second end 116, and the body 112 supports a user ID member 120. The user ID member 120 may include one or more identification technologies such as an RFID device that may be embedded within the central or other portion of the body 112. In some cases, the user ID member 120 may instead or additionally be a central decoration/graphic support member or support other or additional functional devices (such as a timepiece, a pedometer, a GPS device, and so on). The shape of the body 112 is defined by an outer edge 118 that extends about the periphery of the body 112 (or at least the top and bottom edges of the body 112), and, as shown, the body 112 may be rectangular (when in a flat or planar configuration as may the case prior to assembly) or the body 112 may have an arcuate shape or curved shape as shown from end 114 to end 116.

The body 112 also includes a portion of a coupling or interconnecting mechanism used to connect or lock it to adjacent/overlapping sizing assembly 130, and the coupling or interconnecting mechanism is provided in part by the configuration of endwall or sidewall 115 proximate to the end 114 of body 112 and of endwall or sidewall 117 proximate to the end 116 of body 112. The configuration of these sidewalls 115, 117 for example may provide half of a tongue and groove or similar interconnection device that may be coupled with a corresponding other half of a tongue and groove or other interconnection device provided by the end or sidewalls 148 and 156 of abutting portions or segments 142 and 152 of the band sizing assembly 130.

The band assembly 100 also includes a second portion in the form of a band sizing assembly 130 that can be selectively coupled to the ends or sidewalls 115, 117 of the base band element body 112 as part of sizing or personalizing the band assembly 100. As shown, the band sizing assembly 130 includes a number of sizing segments that can be chosen and interchanged by a user and then coupled together at their ends/sidewalls to form a single sizing band that may then be coupled to the base band element 110 to form the wearable band 100 shown in FIGS. 1A and 1B. In the illustrated example, the band sizing assembly 130 includes three sizing segments: a central or middle sizing element 132 and two outer sizing elements 142, 152. The middle sizing element 132 includes a body 134 defined in part by upper and lower edges 135 and in part by ends or sidewalls 138, 136, which are configured for coupling/interconnecting with other sizing segments in the band sizing assembly 130 and/or with base band element 110. The outer or additional sizing segments 142, 152 also include bodies 144, 154 defined in part by upper and lower edges 145, 155 and by ends or sidewalls 146, 148, 156, 158, which are also configured for coupling/interconnecting with other sizing segments in the band sizing assembly 130 and/or with base band element 110.

The specific interconnection or coupling mechanism provided at the interface or joint between the bodies 112, 134, 144, 154 may be varied to practice the invention, with tongue and groove or similar sliding connections being shown in some of the following figures as one useful but non-limiting example. Significantly, though, the band assembly 100 may be assembled by an end user or wearer without the use of tools by simply sliding or otherwise connecting or linking the ends or sidewalls of adjacent bodies of the segments or base band body 112. For example, the body 154 of sizing segment 152 may be separated from the body 112 at the interface of the sidewalls 117 and 156 simply by pulling "upward" on the body 154 when the assembly 100 is in the position shown in FIGS. 1A and 1B, and reassembly would involve sliding or coupling the two ends or sidewalls 117, 156 back together by pushing "downward" on the body 154 (or otherwise providing such relative movement between the bodies 112, 154 with the sidewalls 117, 156 in coupling positions or proximity).

In FIGS. 1A and 1B, the assembly 100 is sized by including three sizing segments 132, 142, 152, and, further, the segment 132 may be a first size or length that is greater than the two similarly sized segments 142, 152. For example, it may be determined that it would be desirable to add a particular length to the length of the base band element body 112 to size the assembly 100 to a person's wrist, and the segments 132, 142, 152 would be chosen such that their combination of lengths provides the desired additional length. In one particular case, the middle segment 132 may provide half of this added length while the other half of this added length may be provided by the combined lengths of the two sizing segments 142, 152, which may be equal in length such that each provides one fourth of the added length. In practice, the sizing segments 142, 152 may be of differing lengths to achieve a different length for the sizing assembly 130 that may be added to the length of the base band element body 112. Further, the band sizing assembly 130 may include more sizing segments (not shown in FIGS. 1A and 1B) or fewer sizing segments, and the segments 132, 142, 152 shown may be replaced by other segments to size the assembly 100 in a particular way and/or to personalize/customize the look and feel of the wearable band assembly 100.

The bodies 112, 134, 144, 154 may be formed of the same or differing materials, and these materials may vary to implement the assembly 100. In some embodiments, the bodies are formed of a plastic, a rubber (e.g., a silicone or the like), or similar material that may be relatively rigid but still be comfortable to wear and also be flexible to facilitate coupling of the ends or sidewalls (115/148, 138/146, 136/158, 117/156) at the mating points between bodies. In some embodiments, each of the bodies has a generally uniform thickness (e.g., up to 1 mm to several mm or the like) and may be generally planar prior to assembly into the loops to be placed upon a wrist or other portion of a user's body. For example, each body may generally take the shape of a relatively thin rectangle formed of a flexible material that can be bent to form the loop of assembly 100 shown. In some cases, though, one or more of the bodies may be more rigid and include an arched or arcuate shape. For example, the body 112 may be thicker in the user ID member 120 or central portion, which may make it more rigid than the other bodies 134, 144, 154, and the body 112 may be shaped as a semicircle or similar shape to better fit a person's wrist.

FIG. 2 illustrates a tape measure 210 that may be used by a wearer to determine or measure their wrist size. The tape measure 210 includes markings 212 that indicate the measured size when the tape measure 210 is wrapped about the wrist and aligned with the end of the tape measure 210. As shown, in a human population, the smallest wrist size is typically about 90 millimeters (mm) while the largest wrist size is over 200 mm (such as about 260 mm or more). In one embodiment, the band assembly 100 may be provided or shipped with the tape measure 210, and the user/wearer may use the tape measure to determine their wrist size. The measured wrist size may then be used to determine the overall length desired for wearable band assembly 100, and the user may add one or more sizing segments from a band sizing assembly 130 such that the band assembly 100 is properly sized when these sizing segments are linked together and coupled at the exposed edges/sidewalls to the base band element body 112.

In this regard, graph 220 illustrates exemplary groups 222, 224, 226 that may be provided for a band assembly 100 for a typical human population. In this example, the band assembly 100 is a wristband or segmented bracelet and graph 220 represents differing wrist sizes for which it is desirable to provide a band assembly 100 that has user-adjustable size. As shown, a first group 222 that typically includes children and adults with smaller wrists is shown (e.g., wrists of about 100 to 130 mm or the like). In the band assembly 100, the combination of the base band 110 and one (or two or more in some cases) of the sizing segments of a band sizing assembly (e.g., the sizing segment 132 may be adapted for coupling to the sidewalls 115, 117 of body 112 of the base band element) may be configured in size/length to provide an assembly 100 with a length covering this first group.

A second group 224 may be defined or selected to include a range of "average" teens and adults. For example, the second group 224 may range from about 130 mm (or some number smaller to provide overlap with group 222 such as 125 mm) to about 190 mm or the like, and a second band sizing segment or link may be included in the sizing assembly 130 that is added to base element body 112. In this manner, the combination of the base band 110 and sizing assembly 130 may have a length that is chosen to allow the band assembly 100 with coupled bands 110, 130 to be worn by individuals having a wrist size between 130 and 190 mm (or other lower and upper bounds). Since the band 100 is of a fixed size once assembled (cannot be tightened or loosened although the band 130 may have some elasticity such as when the bodies of the sizing segments are formed of a rubber or a soft plastic or the like), subsets of each group 222, 224, 226 may also be covered such as by adding one or more additional sizing segments chosen based on their length to obtain a desired fit for a user's wrist.

Finally, in this example, a third group 226 may be defined to include people with larger wrists such as wrists of 190 mm to 240 mm (or some other lower and upper bounds with the lower bound often being chosen to provide an overlap of the second and third groups 224, 226 such as 185 mm when the second group upper bound is 190 mm). A third band sizing segment may be provided in the sizing assembly 130 that is designed or chosen such that the assembly 100 now has a greater length such that this length allows people with wrist sizes falling in the third group 226 to wear the band assembly 100. In some cases, though, this could be achieved by using two sizing segments with one or both being relatively long or by using four or more sizing segments of various lengths. Again, the sizing assembly 130 may be lengthened by adding additional segments or replacing an existing segment with a longer one. In this manner, the band sizing assembly 130 is useful for allowing a user to size the wearable band assembly 100 to a desired size, which may be any of a number of sizes falling over a relatively large range, with some embodiments imposing no upper limit on size (e.g., diameter of the formed loop or band 100).

FIG. 3 illustrates the use of the band assembly 100 in one configuration 310 to provide a band with a length sized to the particular wrist 312 and its diameter/size, $D_{wrist}$. In configuration 310, the band assembly 100 may be configured as shown in FIG. 1 to include three sizing segments 132, 142, 152 to provide an extension in length with sizing assembly 130. The segments 132, 142, 152 are coupled or linked together via interconnection or coupling mechanisms provided by their sidewalls (e.g., tongue and groove arrangements or the like), and the sizing assembly 130 is coupled to the base band 110 via an interconnecting or coupling mechanism provided by the exposed sidewalls of the sizing assembly 130 and the sidewalls or ends of the base band element 110.

The band assembly 100 may be resized to suit differing wrist sizes by adding one or more sizing segments to the band sizing assembly 130 (e.g., to suit larger wrists 312) or to suit a second group of wrist sizes (a range of smaller wrist sizes) by removing one or more of the band sizing segments from the band sizing assembly 130. In any of these configurations of the band 100, the base band element 110 is retained or used such that the user ID member 120 is included in the assembly 100 and worn on the wrist 312. In this manner in embodiments where the band assembly 100 provides user identification, the ID technology element 120 within base band element 110 is included in the band 100 in all configurations of the assembly 100 as is at least one of the sizing segments of the sizing assembly 130. In some embodiments, the sizing assembly 130 or one or more of its sizing segments may be exchanged or interchanged by the wearer for non-standard or original elements so as to customize the look to suit the wearer and/or to provide a differing sized assembly 100 (e.g., replace a segment with a first length (such as 20 mm) with a segment with a second differing length (such as a shorter segment (10 mm in length) or longer segment (30 mm or more in length in this example)).

Figure 4:
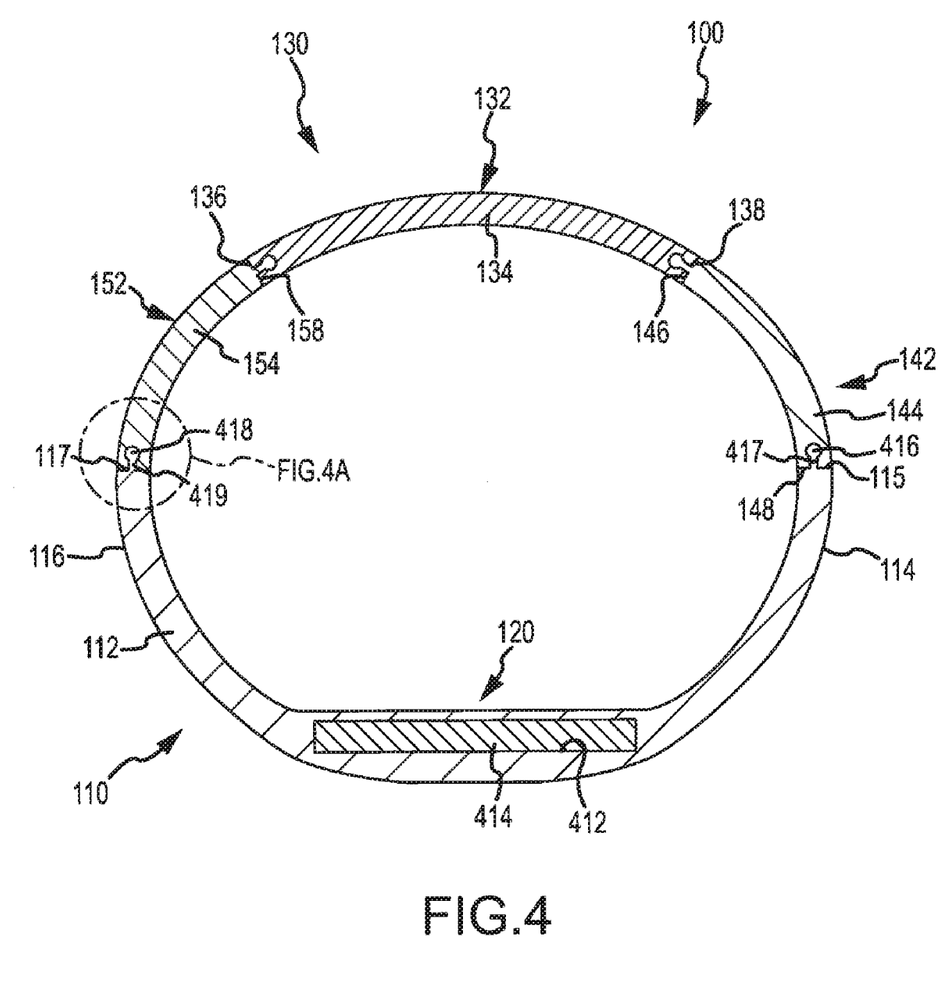
FIG. 4 is a sectional view of the band assembly of FIG. 3 taken along line 4-4 illustrating a tongue and groove interlocking or coupling mechanism in sidewalls/ends for linking adjacent pairs of the segments and the base band element (e.g., the sidewalls of these components each include a tongue or a groove allowing the sizing segments to be interchanged readily to accurately size the band assembly as the segments may have differing sizes/lengths as shown)
Figure 4A:
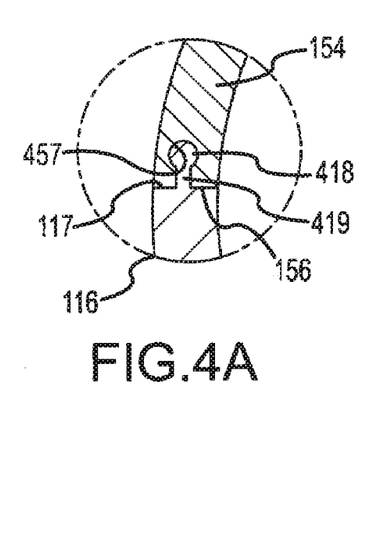

FIG. 4 is a sectional view of the band assembly 100 shown in FIG. 3 taken along line 4-4 illustrating a tongue and groove interlocking or coupling mechanism in sidewalls/ends for linking adjacent pairs of the segments 132, 142, 152 and the base band element 120. In general in this embodiment, the sidewalls of these components each include a tongue or a groove allowing the sizing segments to be interchanged readily to accurately size the band assembly as the segments may have differing sizes/lengths as shown.

The base band 110 has a body 112 with a first length that when combined with the length of the sizing band assembly 130 helps to define the overall length of the band assembly 100. The body 112 may be an elongated strip with an outer shape defined by the outer wall/edge 118 with a width and a thickness extending from a first end 114 to a second end 116. The width and thickness may be relatively uniform between the ends 114, 116 or it may vary such as in a center portion in which a user ID member 120 is provided. In this center portion, the body 112 may be thicker and/or wider such as to provide room in the user ID member 120 for a chamber 412 for receiving or retaining user identification technology device 414 such as, but not limited to, an RFID module or chip that may be configured to store user ID data and other data linked to the user (e.g., rights to access or use a facility or the like).

The sidewalls or edges 115, 117 of the body 112 near the ends 114, 116 are configured for interlocking with the band sizing assembly 130 and its segments 132, 142, 152. As shown, the interlocking or coupling mechanism may be provided using a tongue and groove arrangement with the tongue or groove provided on each of the sidewalls 115, 117, with each sidewall containing the same or a different one of these components (e.g., wall 115 may have a groove while wall 117 may have a post or tongue). As shown in the enlarged view of the coupling in the assembly 100, the sidewalls 115, 117 are adapted with a tongue or post 416, 418 which is spaced apart from the sidewalls 115, 117 some desired distance via extension or spacer wall 417, 419.

To allow coupling with the base band element body 112, the sizing segments 142, 152 each include a groove or slot in their sidewalls or mating edges 148, 156 for receiving the posts/tongues 416, 418. This can be seen in the enlarged view which shows the sidewall 156 of segment 152 including a groove 457 in body 154 that is configured in shape (or cross section) and size (e.g., diameter and offset similar to extension 419) to receive the tongue 418 and extension 419. The sizing may be such that a press or interference fit is provided to retain the connection while in other cases the groove 457 may be somewhat larger in size to more readily receive the tongue/post 418 with other devices used for providing a snap or lock connection (such as a rib or raised surface provided on tongue 418 and a recessed surface provided in the groove 457 to lock the bodies 112, 154 together when in a desired relative position).

FIG. 4 also shows that the sizing segments 132, 142, 152 may include interlocking mechanisms on their edges or sidewalls for coupling with adjacent ones of the segments 132, 142, 152 within the band sizing assembly 130. In some cases, the interlocking mechanisms are configured to allow nearly any ordering of the segments 132, 142, 152 in the assembly 130 relative to each other and relative to the mating with the sidewalls 115, 117 of the base band element body 112. However, in the embodiment of assembly 100 shown in FIG. 4, the middle or central sizing segment 132 is provided with groove connections on both of its sidewalls 138, 136, but the outer segments 142, 152 are shown to have grooves on one edge or sidewall 148, 156 and a tongue/post on the other edge or sidewall 146, 158 for coupling with the center or middle sizing segment 132.

The segments 132, 142, 152 may be readily slid together and apart by a user to assemble the band sizing assembly 130 and then to join it with the base band element 110. To adjust the sizing of the assembly 130 (and, therefore, the band assembly 100), the user may replace the center or middle sizing segment 132 with one that has a greater length but similar end connections to increase the size and with one that has a shorter length but similar end connections to decrease the size. Alternatively, one or more additional end segments with similar end connections in its sidewalls may be added (on either side of middle or center segment 132) to increase the size of the assembly 130 (and assembly 100). In other cases, a segment with a smaller or greater length may be substituted for one or both of the outer segments 142, 152 to alter the size of the band sizing assembly 130 (and assembly 100). As will be appreciated, a user may use this segmented band assembly 100 to provide a desired size to suit their wrist (or other body part such as amide or neck) by selecting a set of sizing segments and assembling these components to create an assembly 100 with a user-selectable size (without requiring use of tools for assembly or disassembly).

Figure 5:
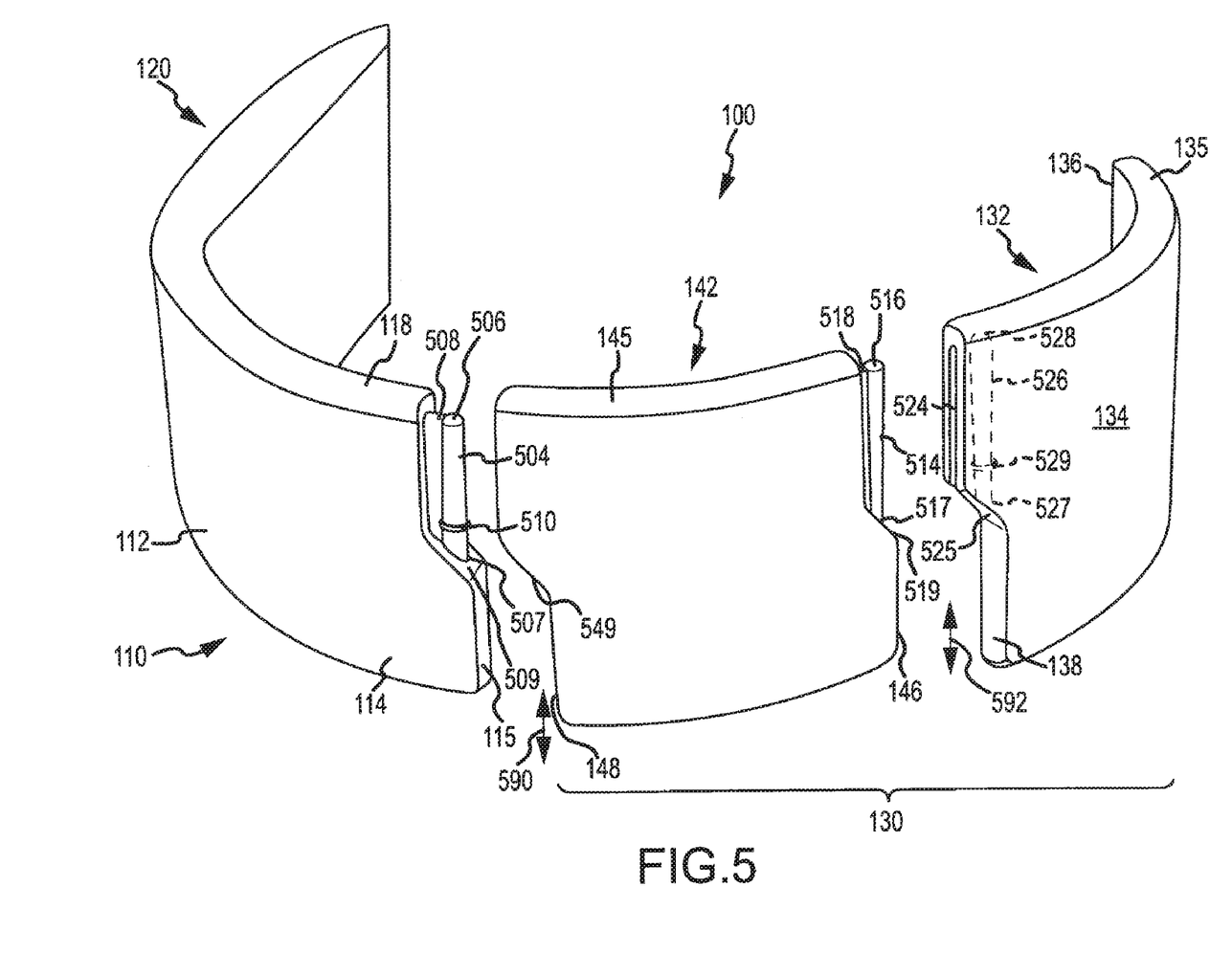
FIG. 5 illustrates a partial exploded or disassembled view of the band assembly of FIGS. 1A and 1B illustrating in detail one interconnection or coupling mechanism that may be provided via the design of the segment and base band element body sidewalls.

The interconnection mechanism such as the tongue and groove arrangement shown in FIG. 4 may extend the entire height of the segment and base band element body sidewalls or it may only be provided for a portion or fraction of the overall sidewall height as shown in some of the exemplary embodiments such as in FIG. 5. In the assembly 100 shown in FIG. 5, the base band element body 112 includes a sidewall 115 near its end 114 that is configured to provide the tongue or post portion of a tongue and groove interlocking mechanism. It is also adapted to provide a stop to prevent a linked sizing segment from sliding its entire length (e.g., a stop about midway or some other portion of the overall height of the sidewall 115). Further, the sidewall 115 is adapted to provide a snap or lock retention of the received sizing segment so as to require at least some amount of force (e.g., a "vertical" force or force along the longitudinal axis of the tongue/groove) to disassemble linked components of the assembly 100.

Specifically, the sidewall 115 includes an elongated post or tongue 504 that extends from a first or inner end 507 to a second or outer end 506. The tongue 504 may be positioned a distance from the body 112 via an extension 508, and the tongue 504 may extend from a stop or receiving surface 509 to the second end 506, which may be flush with edge/sidewall 118 or somewhat recessed/offset. The tongue 506 may be circular in cross sectional shape with a longitudinal axis extending transverse or even perpendicular (as shown) to the longitudinal axis of the base band element body 112.

The stop or receiving surface 509 in sidewall 115 may extend outward from the body 112 in a direction parallel to the longitudinal axis or, as shown, transverse to this axis, e.g., to provide an angled stop surface (e.g., 120 to 150 degrees as measured from lead surface that initially receives the sizing segment to the stop 509). To provide a snap fit, the tongue may have a rib or raised surface 510 at or near the end 507 near the surface 509, and the groove in sidewall 148 may include a similar or corresponding recessed receiving surface with a larger diameter such that when the post or tongue 504 is inserted into the groove in sidewall 148 the rib 510 and recessed surface mate and snap/lock the body 112 to the sizing segment 142. The sidewall 148 includes a stop or receiving surface 549 that abuts the surface 509 when the bodies 112, 144 are linked or fit together as shown with arrow 590.

The sidewall 146 of the sizing segment 142 may be configured similarly to the sidewall 115 with a tongue/post 514 extending from a first, inner end 517 to a second, outer end 516. The sidewall 146 may include a stop or receiving surface 519 some distance from the edge 145 of body 144 (e.g., about halfway along the length or height of sidewall 146), and this receiving surface 519 may also extend parallel to the longitudinal axis of the body 144 or as with receiving surface 509 extend at an angle such as 120 to 150 degrees from the leading portion of sidewall 146 receiving or mating with another sizing segment (such as segment 132 as shown with arrow 592). The post 514 may be circular in cross sectional shape and be set apart from the body 144 by an extension or positioning wall 518. As shown, the sizing segment 142 includes a first end or sidewall 148 with a groove (or first half of an interlocking mechanism) and a second end or sidewall 146 with a tongue/post (or second half of the interlocking mechanism).

The sizing segments of a band sizing assembly 130 may be assembled or disassembled as shown with arrow 592. In this case, the inner or center sizing segment 132 includes a sidewall 138 that includes a stop or receiving surface 525 for abutting and mating with stop or receiving surface 519 in the sidewall 146 (or with surface 509 if the segment 132 were to be positioned against base band element 110). The stop surface 519 includes an opening to a slot or opening 524 for receiving the extension 518 of segment 142 and also an opening to a groove 526 in sidewall 138 that extends from a first, outer end 527 to a second, inner end 528. The groove 526 may be circular in cross section (or other shape) to match the shape of the post or tongue 514. The groove 526 typically will have a length or depth that matches or exceeds the length or height of post 514 such that the segment 142 may be fully received in segment 132 with stop surfaces 519, 525 in contact when assembled as shown with arrow 592. To provide a snap fit, the groove 529 may include a recessed surface 529 to receive a rib in post 514 (such as a rib similar to rib 510 in post/tongue 504), and the recessed surface 529 may be located near the opening to groove 526 near end 527 such that the snap fit is provided when the post/tongue 514 is fully inserted into groove 526 (with surfaces 519, 525 in contact).

The posts/tongue members 504, 514 and corresponding grooves (such as groove 526) may have a relatively uniform shape and size along their lengths or vary to provide a desired fit or linking of the components of assembly 100. For example, as shown with post/tongue member 504, the circular cross section may be smaller at the outer (or initial engagement) end 506 and increase in size/diameter toward the end 507. The groove in sidewall 148 would be tapered in a similar but opposite manner to receive the tapered post 504. A tapered diameter or increasing size in the cross section of the tongue (and decreasing size of the groove) may be more desirable in embodiments that do not include the stop/receiving surfaces 509, 519, 525, 549, as the tapering may be useful to provide a stopping effect for linked components in the assembly 100.

Figure 6:
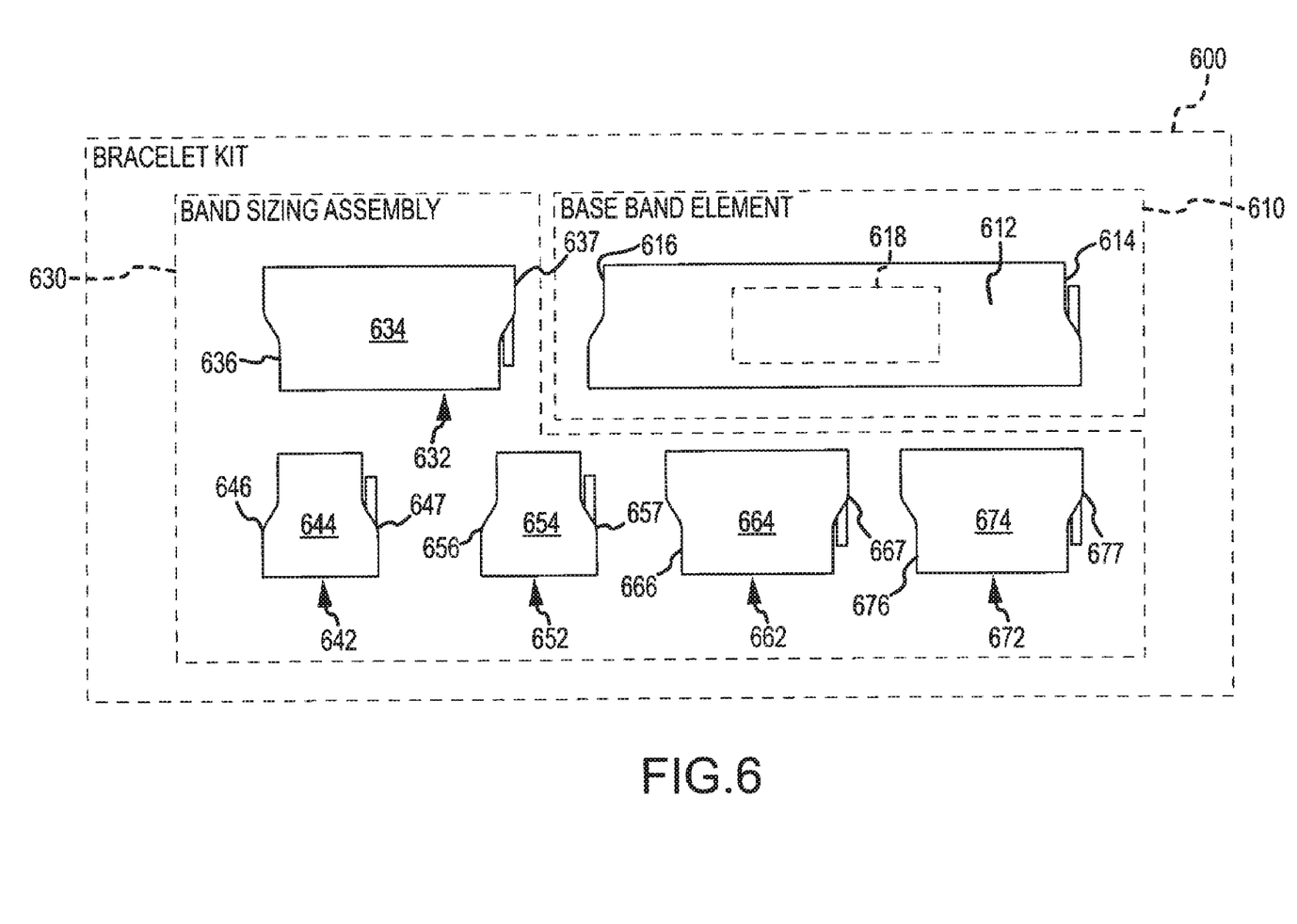
FIG. 6 shows a user ID bracelet kit that may be provided to a user/wearer according to an embodiment of the invention illustrating a base band element along with a number of sizing segments that may be provided in a band sizing assembly to allow a user to assemble a band with a particular size and/or with a particular look (e.g., two segments may be interchangeable with reference to size/length and coupling configuration but differ in appearance and/or material)

A bracelet assembly or kit 600 may be provided to a user or wearer as shown in FIG. 6 such that the user may readily size a bracelet to their wrist (or other body part) size and/or may readily choose similarly sized but differently designed (in appearance, material, or other characteristics) band elements to personalize their bracelet. The bracelet kit 600 is shown to include a base band element 610 that includes an elongated, generally rectangular body 612 that may be a relatively thin (e.g., up to several millimeters in thickness) and have a uniform width (but this is not required). The body 612 extends from a first endwall 614 to a second endwall 616, and, in this embodiment, the first endwall or sidewall 614 is adapted to provide a post/tongue portion of a bracelet interlocking or coupling mechanism (e.g., the male portion) while the second endwall or sidewall 616 is adapted to provide a groove or slot portion of the interlocking mechanism (e.g., the female portion). The body 612 may further include a user ID member 618, e.g., an embedded RFID tag or the like. The body 612 has a length as measured along its longitudinal axis that typically is some amount smaller than a smallest wrist size for a particular population, and, hence, one or more sizing segments preferably are added to the base band element body 612 to form a bracelet for a user to wear.

To this end, the bracelet kit 600 includes a band sizing assembly 630 that includes a number of sizing segments of varying lengths that are adapted with the design of the endwalls or sidewalls to interlock with each other and with base band element body 612 to form a bracelet of a particular length (or circumference when formed into a loop). As shown, the sizing assembly 630 includes five sizing segments 632, 642, 652, 662, and 672 to allow a user to create bracelets of various sizes and appearances.

Figure 7A:
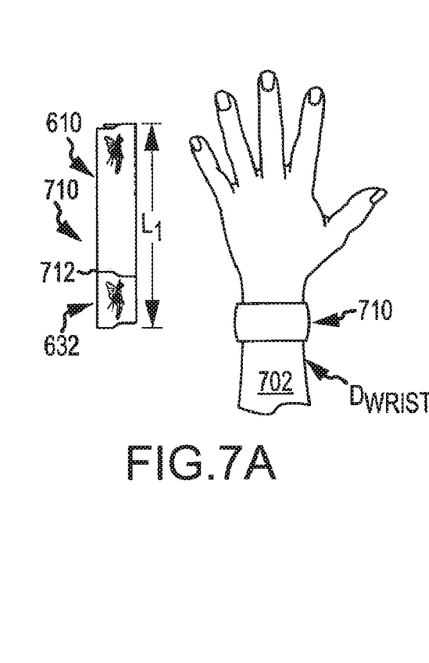
FIGS. 7A to 7C show three embodiments of band assemblies that may be formed using the components of the user ID bracelet kit shown in FIG. 6 so as to size the band assemblies to three wrists having differing sizes (a smaller wrist falling in the range/group of small wrists, a larger wrist falling in the range/group of medium-sized wrists, and a larger wrist falling in the range/group of relatively larger wrists as may be seen in FIG. 2 for example).

For example, the first extension or sizing segment 632 has a body 634 with a length as measured from sidewall 636 to sidewall 637, and this length when combined with the length of the base band element body 612 may provide an overall assembly or bracelet length, $L_1$, as shown in FIG. 7A. The sidewall 637 includes a post or tongue for mating (as shown by junction/interconnecting interface 712) with the groove in sidewall 616 of the base band element body 612 while the sidewall 636 includes a groove for coupling with the post/tongue of sidewall 614 of body 612 to allow a bracelet 710 to be formed. The bracelet 710 may be worn on a wrist 702 with a relatively small diameter, $D_{wrist}$, such as a wrist size falling within a smaller wrist size range 222 as shown in FIG. 2.

The band sizing assembly 630 further includes a pair of sizing segments 642, 652 that have bodies 644, 654 of identical length as measured from first ends 646, 656 (which are adapted with grooves for mating with a tongue or post) to second ends 647, 657 (which are adapted with tongues/posts for mating with a groove or slot on another segment or body 612). The length of the bodies 644, 654 differs from the body 634 of the first sizing segment 632 and may be shorter as shown in FIG. 6. A medium length sizing segment may be provided with the sizing segments 662, 672 which have bodies 664, 674 having lengths as measured from first ends 666, 676 (which are adapted with grooves/slots for mating with tongue/post of other segments or body 612) to second ends 667, 677 (which are adapted with post/tongue for coupling with grooves or slots provided on sidewalls of other segments or body 612). The length of the elements 662, 672 may be less than the length of first sizing segment 632 but greater than the length of the sizing segments 642, 652. In this manner, the bracelet kit 600 may be used to form a wide variety of bracelets of differing look and feel and also differing sizes (as may be defined by the overall length of the segments and body 612 and/or by a circumference of fully interconnected bracelet).

Figure 7B:
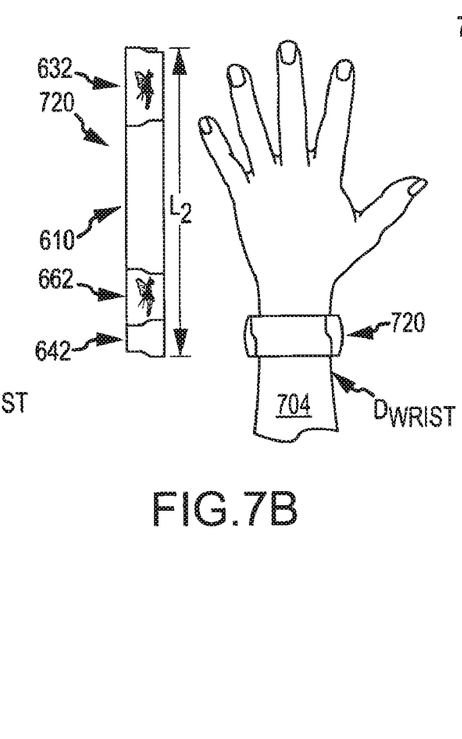

For example, as shown in FIG. 7B, a bracelet 720 may be formed that includes first sizing segment 632 but also segment 662 and segment 642. In other words, the first segment 632 is included but so are one of the smaller segments 642, 652 and one of the medium sized segments 662, 672. In this manner, a bracelet 720 is provided by linking the sizing segments 632, 642, and 662 together (via their sidewall configurations) to provide a band sizing assembly, and this assembly is then linked or interconnected (again, via the sidewall configurations of the sizing segments and the base band element body 612) to provide a desired overall bracelet length, $L_2$. This length, $L_2$, may be used by a group of people with medium sized wrists 704 with a particular wrist diameter that falls within a second group 224 of a user population wrist sizes, for example. The length, $L_2$, as shown is larger than the first length, $L_1$.

Figure 7C:
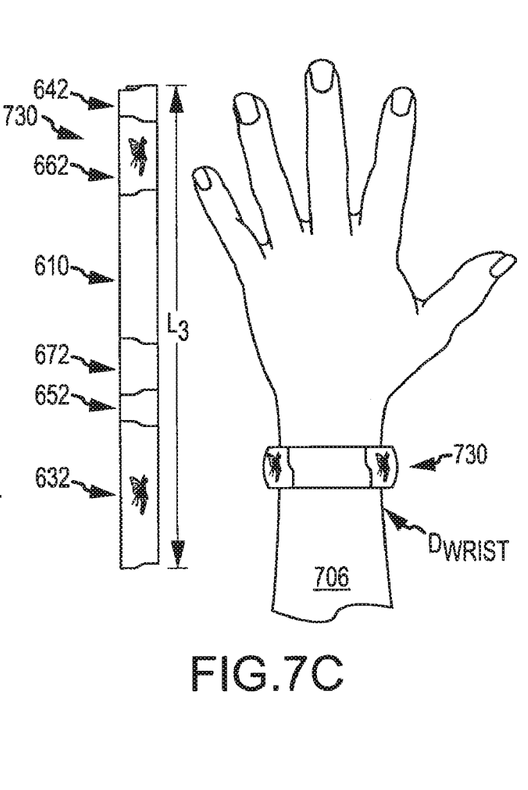

As another example, the kit 600 may be used to assemble a third bracelet 730 for a third, larger wrist 706 (e.g., one with a diameter, $D_{wrist}$, that falls within a third group 226 corresponding to a portion of the user population with relatively large wrists). To this end, the bracelet 730 is formed by including all five of the sizing segments 632, 642, 652, 662, and 672 to provide the maximum length, L3, for the particular kit 600. Note, the particular order of the sizing segments may be varied in bracelet 730 such that a user can achieve some personalization simply by choosing the order in which the segments are combined such as when the segment bodies have differing graphical designs, colors, or the like.

The above described invention including the preferred embodiment and the best mode of the invention known to the inventor at the time of filing is given by illustrative examples only. It will be readily appreciated that many deviations may be made from the specific embodiments disclosed in the specification without departing from the spirit and scope of the invention.

We claim:

1. A wearable band assembly with an adjustable length, comprising:

a base band element with a body extending a first length from a first sidewall to a second sidewall, wherein the body comprises a user identification member adapted to store user identification information; and a band sizing assembly comprising at least one band sizing segment, wherein the band sizing assembly extends a second length from a first sidewall to a second sidewall, wherein the first and second sidewalls of the band sizing assembly are configured for coupling with the first and second sidewalls, respectively, of the base band element body to form a closed loop and to define a third length associated with a circumference of the closed loop, wherein the coupling between the first sidewalls and the second sidewalls comprises a tongue and groove connection with one of the first and one of the second sidewalls comprising a tongue extending therefrom and one of the first and one of the second sidewalls comprising a groove for receiving the tongue, wherein the tongues and the grooves extend transverse to the longitudinal axis of the base band element body and have circular cross sectional shapes, wherein the circular cross sectional shape of each of the tongues is tapered with a diameter that increases from a first end to a second end, and wherein the circular cross sectional shape of each of the grooves is tapered opposite the tongues with a diameter that decreases from a first end to a second end.

2. The band assembly of claim 1, wherein each of the tongues includes a raised rib and wherein each of the grooves includes a recessed surface for receiving the raised rib when one of the tongues is inserted into the groove.

3. The band assembly of claim 1, wherein each of the sidewalls comprises a stop surface extending outward, whereby pairs of the stop surfaces are placed in abutting contact when the famed base band element body is coupled with the sizing segments of the band sizing assembly.

4. The band assembly of claim 1, wherein the band sizing assembly comprises a first sizing segment and a second sizing segment and wherein the first sizing segment is detachably engaged with the second sizing segment and has a body with a length that differs from a length of a body of the second sizing segment.

5. The band assembly of claim 4, wherein the detachable engagement is provided by a two-piece tongue and groove connection mechanism with a first part provided on a sidewall of the first sizing segment and a second part provided on a sidewall of the second sizing segment, whereby the sidewalls of the first and second sizing segments are linked together with the tongue and groove connection mechanism.

6. The band assembly of claim 4, wherein the band sizing assembly comprises at least a third sizing segment detachably engage with the first or second sizing segment and wherein the third sizing segment has a body with a length differing from the lengths of the first and second sizing segment bodies.

7. The band assembly of claim 1, wherein the user identification member comprises a radio frequency identification (RFID) tag.

8. An identification band, comprising:
a base band comprising a substantially planar body extending between a first sidewall and a second sidewall;
a user ID member provided in the base band body; and
a band sizing assembly comprising a plurality of sizing segments of at least two differing lengths, wherein at least one of the sizing segments is linked to the first and second sidewalls of the base band to form a closed loop via tongue and groove connections,
wherein a first one of the sizing segments is linked to the first sidewall of the base band, wherein a second one of the sizing segments is linked to the second sidewall of the base band, and wherein the first and second ones of the sizing segments are linked together at sidewalls distal to the base band via a tongue and groove connection, and
wherein each of the sidewalls comprises a stop surface extending outward from and transverse to the corresponding one of the sidewalls, whereby mating pairs of the stop surfaces are placed in abutting contact when the base band body is coupled with the sizing segments and when the first and second sizing segments are linked together.

9. The band of claim 8, wherein the user ID member comprises an RFID device.

10. The band of claim 8, further comprising a third one of the sizing segments interposed between the first and second ones of the sizing segments and wherein the first, second, and third ones of the sizing segments have at least two differing lengths.

11. A wearable band, comprising:
a base band element with an elongated body defined by spaced apart first and second endwalls, the body including a user ID member storing data identifying a wearer of the band;
a first sizing segment with first and second sidewalls, the first sidewall detachably linked to the first endwall of the base band element body via a tongue and groove connection;
a second sizing segment with first and second sidewalls, the first sidewall detachably linked to the second sidewall of the first sizing segment via a tongue and groove connection; and
a third sizing segment with first and second sidewalls, the first sidewall detachably linked to the second endwall of the base band element body via a tongue and groove connection and the second sidewall detachably linked to the second sidewall of the second sizing segment, whereby a closed loop is formed containing the base band element, the first sizing segment, the second sizing segment, and the third sizing segment,
wherein the detachable linking between the sizing segments is provided by tongue and groove connections, and
wherein each of the sidewalls comprises a stop extending outward from and transverse to the corresponding one of the sidewalls proximate to a base of a tongue of the tongue and groove connection, whereby mating pairs of the stops abut when the base band element body is linked with the sizing segments and when the sizing segments are linked together so to limit travel of one each of the tongues in the tongue and groove connections.

12. The wearable band of claim 11, wherein the first sizing segment has a first length as measured between the first and second sidewalls of the first sizing segment, the second sizing segment has a second length as measured between the first and second sidewalls of the second sizing segment that is greater than the first length, and the third sizing segment has a third length as measured between the first and second sidewalls of the third sizing segment that is greater than the second length.

13. The wearable band of claim 11, further comprising a fourth sizing segment interposed between the second and third sizing segments and detachably linked to both the second sizing segment and the third sizing segments.

14. The wearable band of claim 13, further comprising a fifth sizing segment interposed between the second and fourth sizing segments and detachably linked to both the second sizing segment and the fourth sizing segment.

15. The wearable band of claim 14, wherein the first, second, third, fourth, and fifth sizing segments each have bodies and the bodies of the sizing segments have at least three differing lengths.

16. A wearable band assembly with an adjustable length, comprising:
a base band element with a body extending a first length from a first sidewall to a second sidewall, wherein the body comprises a user identification member adapted to store user identification information; and a band sizing assembly comprising at least one band sizing segment, wherein the band sizing assembly extends a second length from a first sidewall to a second sidewall, wherein the first and second sidewalls of the band sizing assembly are configured for coupling with the first and second sidewalls, respectively, of the base band element body to form a closed loop and to define a third length associated with a circumference of the closed loop, wherein the coupling between the first sidewalls and the second sidewalls comprises a tongue and groove connection with one of the first and one of the second sidewalls comprising a tongue extending therefrom and one of the first and one of the second sidewalls comprising a groove for receiving the tongue, wherein the tongues and the grooves extend transverse to the longitudinal axis of the base band element body and have circular cross sectional shapes, wherein each of the tongues includes a raised rib, and wherein each of the grooves includes a recessed surface for receiving the raised rib when one of the tongues is inserted into the groove.

17. The band assembly of claim 16, wherein each of the sidewalls comprises a stop surface extending outward, whereby pairs of the stop surfaces are placed in abutting contact when the based band element body is coupled with the sizing segments of the band sizing assembly.

18. The band assembly of claim 16, wherein the band sizing assembly comprises a first sizing segment and a second sizing segment and wherein the first sizing segment is detachably engaged with the second sizing segment and has a body with a length that differs from a length of a body of the second sizing segment.

19. The band assembly of claim 16, wherein the user identification member comprises a radio frequency identification (RFID) tag.

* * * * *